US009492619B2

(12) United States Patent
Raab

(10) Patent No.: US 9,492,619 B2
(45) Date of Patent: Nov. 15, 2016

(54) ASSEMBLY FOR A DRUG DELIVERY DEVICE AND DRUG DELIVERY DEVICE

(75) Inventor: Steffen Raab, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1018 days.

(21) Appl. No.: 13/575,352

(22) PCT Filed: Feb. 2, 2011

(86) PCT No.: PCT/EP2011/051446
§ 371 (c)(1),
(2), (4) Date: Oct. 23, 2012

(87) PCT Pub. No.: WO2011/095503
PCT Pub. Date: Aug. 11, 2011

(65) Prior Publication Data
US 2013/0046248 A1    Feb. 21, 2013

(30) Foreign Application Priority Data

Feb. 2, 2010    (EP) .................................... 10152344

(51) Int. Cl.
A61M 5/315    (2006.01)

(52) U.S. Cl.
CPC ..... *A61M 5/31585* (2013.01); *A61M 5/31541* (2013.01); *A61M 5/31555* (2013.01); *A61M 5/31593* (2013.01)

(58) Field of Classification Search
CPC ................... A61M 5/31541; A61M 5/31555; A61M 5/31585; A61M 5/31593
USPC ........................................................ 604/211
See application file for complete search history.

(56) References Cited

U.S. PATENT DOCUMENTS

| 5,827,232 A | 10/1998 | Chanoch et al. |
| 2006/0247581 A1 | 11/2006 | Pedersen et al. |
| 2007/0197976 A1 | 8/2007 | Jacobs et al. |

(Continued)

FOREIGN PATENT DOCUMENTS

| DE | 102007026556 | 12/2008 |
| EP | 0498737 | 8/1992 |

(Continued)

OTHER PUBLICATIONS

European Search Report for European App. No. 10152344.7 dated Sep. 6, 2010.
International Search Report and Written Opinion for Int. App. No. PCT/EP2011/051446, mailed Jun. 6, 2011.

*Primary Examiner* — Edelmira Bosques
*Assistant Examiner* — Leah Swanson
(74) *Attorney, Agent, or Firm* — McDonnell Boehnen Hulbert & Berghoff LLP

(57) ABSTRACT

An assembly for a drug delivery device comprises a housing, at least one stop feature and at least one blocking member. For setting a dose of a drug, the stop feature is configured to be rotated in a dose setting direction with respect to the blocking member and with respect to the housing. For delivering the set dose of the drug, the blocking member is configured to be axially displaced with respect to the stop feature away from an axial starting position and towards an axial interaction position. When the blocking member is in the axial starting position, the blocking member is axially offset from the stop feature and, when the blocking member is in the axial interaction position, the blocking member is configured to mechanically cooperate with the stop feature such that rotation of the stop feature in the dose setting direction with respect to the housing is prevented.

14 Claims, 5 Drawing Sheets

(56) References Cited

U.S. PATENT DOCUMENTS

2008/0108953 A1    5/2008   Moser et al.
2010/0152671 A1*   6/2010   Raab ................. A61M 5/31555
                                                              604/207

FOREIGN PATENT DOCUMENTS

| EP | 1923085 | 5/2008 |
| WO | 2008/031238 | 3/2008 |
| WO | 2008/138908 | 11/2008 |

* cited by examiner

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/051446 filed Feb. 2, 2011, which claims priority to European Patent Application No. 10152344.7 filed on Feb. 2, 2010. The entire disclosure contents of these applications are herewith incorporated by reference into the present application.

FIELD OF INVENTION

This disclosure relates to an assembly for a drug delivery device and a drug delivery device incorporating such an assembly.

BACKGROUND

In a drug delivery device a piston within a cartridge that contains a drug may be provided. The piston may be displaced with respect to the cartridge for delivering a dose of the drug from the cartridge. It is desirable that the dispensed dose of the drug matches the dose which was previously set by a user as good as possible. That is to say, the device should have a high dose accuracy. In particular, it should be avoided that a dose dispensing action may be triggered when the size of the set dose exceeds the quantity of drug present in the cartridge.

Drug delivery devices are described in documents WO 2008/031238 A1 and US 2007/0197976 A1.

SUMMARY

It is an object of the present disclosure to provide an assembly facilitating provision of an improved drug delivery device, for example a device with high dose accuracy.

This object may be achieved by the subject matter of the independent claim. Further features and advantageous embodiments are the subject matter of the dependent claims.

According to one aspect an assembly for a drug delivery device is provided. The assembly may comprise a housing. The assembly may comprise at least one stop feature. The assembly may comprise at least one blocking member. The assembly may comprise a rotation member. The assembly may comprise a drive member. The rotation member may be configured to rotate in a dose setting direction with respect to the housing for setting a dose of a drug. The rotation member may be configured to rotate in a dose delivery direction with respect to the housing for delivering the set dose of the drug. The drive member may be adapted to follow rotational movement of the rotation member in the dose delivery direction with respect to the housing by mechanical interaction with the rotation member. For setting a dose of the drug the stop feature may be configured to be rotated in the dose setting direction with respect to the blocking member and with respect to the housing. For delivering the set dose of the drug the blocking member may be configured to be axially displaced with respect to the stop feature away from an axial starting position and towards an axial interaction position. When the blocking member is in the axial starting position, the blocking member may be axially offset from the stop feature. When the blocking member is in the axial interaction position the blocking member may be arranged and/or configured to mechanically cooperate with, in particular to abut, the stop feature. By this mechanical cooperation rotation of the stop feature in the dose setting direction with respect to the housing may be prevented.

A further aspect relates to a drug delivery device. The drug delivery device expediently comprises the assembly described above. The drug delivery device comprises a cartridge. The cartridge may hold a plurality of doses of the drug. The assembly may provide an end-stop mechanism for the drug delivery device. The end-stop mechanism may be configured to prevent setting of a dose of the drug which exceeds a quantity of the drug present in the cartridge.

The drug delivery device may be an injection device. The drug delivery device may be a pen-type device, e.g. a pen-type injector. Preferably, the drug delivery device is a device configured to dispense pre-set doses of the drug. The drug may be a liquid medication, such as long-acting or short-acting insulin, heparin or growth hormones.

For setting a dose of the drug the stop feature may be rotated in the dose setting direction with respect to the housing. For delivering the set dose the stop feature may be rotated in a dose delivery direction with respect to the housing. The dose delivery direction may be opposite to the dose setting direction.

In the axial interaction position the blocking member may be positioned at the axial position of the stop feature with respect to the housing such that the blocking member and the stop feature may interact, in particular abut. When the blocking member is in the axial interaction position the whole amount of the drug held in the cartridge which was intended for dispense may have been dispensed. Consequently, dispensing of a subsequent full-size dose of the drug may no longer be possible. In the axial interaction position setting of a subsequent dose of the drug may be prevented due to mechanical cooperation of the stop feature and the blocking member, and hence, underdosing may be prevented. In this way, a user-friendly and safe drug delivery device may be achieved.

According to an embodiment, for delivering the set dose of the drug the blocking member and the stop feature are configured to rotate together in a dose delivery direction with respect to the housing.

According to an embodiment, the blocking member is secured against rotation in the dose setting direction with respect to the housing. Hence, common rotation of the blocking member and the stop feature in the dose setting direction with respect to the housing for setting a dose of the drug may be prevented when the blocking member and the stop feature mechanically cooperate with each other.

In this way, setting of a subsequent dose of the drug, which may exceed the present quantity of the drug held in the cartridge, may be effectively prevented when the blocking member is in the interaction position.

According to an embodiment, the stop feature is rotated about a stop feature angle in the dose setting direction with respect to the housing for setting the dose of the drug. The blocking member may be rotated about a blocking member delivery angle in the dose delivery direction with respect to the housing when the blocking member is displaced from the axial starting position towards the axial interaction position. When the blocking member is in the axial interaction position the angular distance between the blocking member and the stop feature is expediently less than the stop feature angle.

In particular, the minimum rotation angle of the stop feature necessary for setting a minimum dose may be greater than the angular distance between the stop feature and the blocking member in the interaction position. Hence, completion of a further dose setting action is prevented when the blocking member is in the axial interaction position.

Preferably, the stop feature is rotated by less than 360 degrees in the dose setting direction with respect to the housing for setting the dose of the drug.

Preferably, the blocking member is rotated by 360 degrees or more in the dose delivery direction with respect to the housing when being displaced from the axial starting position towards the axial interaction position.

According to an embodiment, when the blocking member is out of the axial interaction position, the stop feature may pass the angular position of the blocking member when being rotated in the dose setting direction.

Hence, when the amount of the drug held in the cartridge exceeds the size of a dose to be set and delivered the stop feature may be rotatable in the dose setting direction with respect to the housing, thereby passing the angular position of the blocking member without mechanical cooperation, in particular abutment, with the blocking member. Thus, setting of at least a minimum dose of the drug is enabled when the blocking member is not in the axial interaction position.

According to an embodiment, the axial interaction position may be defined by the axial position of the stop feature within the housing.

Preferably, when a last dose has been delivered, e.g. when a subsequent minimum settable dose of the drug would exceed the present quantity of the drug in the cartridge, the blocking member has been axially displaced with respect to the stop feature such that the blocking member is positioned at the axial position of the stop feature, i.e. the blocking member overlaps the stop feature. Preferably, axial displacement distance of the blocking member from the axial starting position to the axial interaction position corresponds to the total amount of the drug held in the cartridge.

According to an embodiment, a rotation member is provided. The rotation member may be configured to rotate in the dose setting direction with respect to the housing for setting the dose of the drug. The rotation member may be configured to rotate in the dose delivery direction with respect to the housing for delivering the set dose of the drug. The stop feature may be part of the rotation member. The stop feature may thus rotate when the rotation member rotates.

According to an embodiment, a piston rod is provided. The blocking member may be part of the piston rod. The piston rod may be configured to be axially displaced with respect to the housing for delivering a dose of the drug.

Preferably, the rotation axis runs along the piston rod and, in particular, along a main direction of extent of the piston rod. Preferably, the piston rod is threadedly engaged with the housing. The piston rod may be configured to displace the piston axially with respect to the cartridge for expelling the set dose of the drug from the cartridge.

According to an embodiment, the stop feature protrudes radially, preferably radially inwardly, from the rotation member.

According to an embodiment, the blocking member protrudes radially, preferably radially outwardly, from the piston rod.

According to an embodiment, a drive member is provided. The drive member may be adapted to follow rotational movement of the rotation member in the dose delivery direction with respect to the housing by mechanical cooperation with the rotation member. Rotation of the drive member in the dose delivery direction with respect to the housing may be converted into axial movement of the piston rod with respect to the housing. A stop member may be provided. The stop member may be adapted to prevent rotational movement of the drive member in the dose setting direction with respect to the housing by mechanical cooperation with the drive member, when the rotation member is rotated in the dose setting direction with respect to the housing.

The drive member and the stop member may be coupled, preferably permanently for setting and delivering a dose of the drug, to one another by a uni-directional friction clutch mechanism, for example a slip clutch. The clutch mechanism may be configured to prevent relative rotational movement between the drive member and the stop member during rotation of the rotation member in the dose setting direction. The clutch mechanism may be configured to permit relative rotational movement between the stop member and the drive member during rotation of the rotation member in the dose delivery direction. A resilient member may be provided. The resilient member may provide a force keeping the drive member in engagement, preferably permanent engagement, with the stop member and the rotation member during dose setting and dose delivery.

The drive member and the rotation member may be in, preferably permanent, mechanical contact. The drive member and the rotation member may be coupled, preferably permanently coupled, to one another by a uni-directional friction clutch mechanism. The friction clutch mechanism may be configured to permit relative rotational movement between the rotation member and the drive member when setting a dose of the drug. In this way, rotation of the piston rod and, hence, of the blocking member in the dose setting direction may be effectively prevented. The friction clutch mechanism may be configured to prevent relative rotational movement of the rotation member and the drive member for delivering the set dose of the drug.

The rotation member may be axially moveable with respect to the housing only in a limited fashion. For example, axial movement of the rotation member may be influenced by the configuration of the friction clutch mechanism, e.g. by the depth of teeth of the friction clutch mechanism. Axial movement of the rotation member beyond a given axial distance, which may be determined by the teeth of the friction clutch mechanism, may be limited by means of mechanical cooperation of the rotation member and the housing, for example.

According to an embodiment, the drive member and the piston rod are rotationally locked with each other. Preferably, the piston rod is splined to the drive member.

According to an embodiment, the assembly comprises at least two blocking members. The two blocking members may be oppositely disposed.

According to a preferred embodiment, an assembly for a drug delivery device is provided. The assembly comprises a housing, at least one stop feature and at least one blocking member. For setting a dose of a drug, the stop feature is configured to be rotated in a dose setting direction with respect to the blocking member and with respect to the housing and, for delivering the set dose of the drug, the blocking member is configured to be axially displaced with respect to the stop feature away from an axial starting position and towards an axial interaction position. When the blocking member is in the axial starting position, the blocking member is axially offset from the stop feature and, when the blocking member is in the axial interaction position, the blocking member is configured to mechanically cooperate with the stop feature such that rotation of the stop feature in the dose setting direction with respect to the housing is prevented.

Of course, features described above in connection with different aspects and embodiments may be combined with each other and with features described below.

Further features and refinements become apparent from the following description of the exemplary embodiments in connection with the accompanying figures.

BRIEF DESCRIPTION OF THE FIGURES

Like elements, elements of the same kind and identically acting elements may be provided with the same reference numerals in the figures.

DETAILED DESCRIPTION

Figure 1:
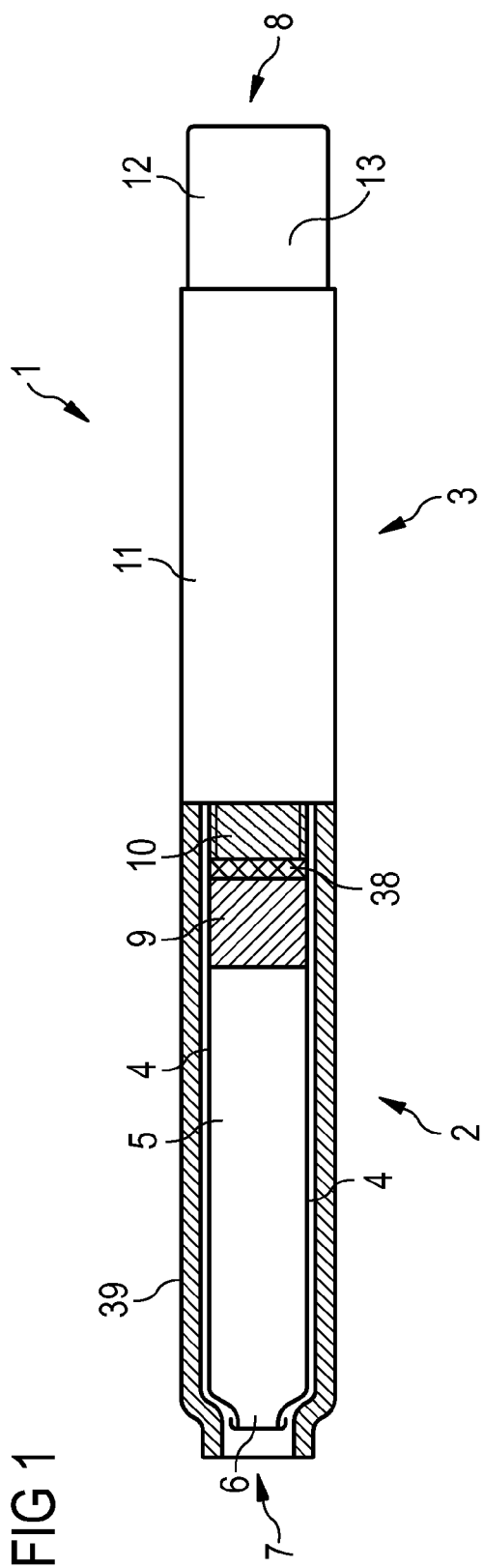
FIG. 1 schematically shows a partly sectional side view of an exemplary embodiment of a drug delivery device, FIG. 2 schematically shows a perspective sectional view of a part of the drug delivery device of FIG. 1, FIG. 3 schematically shows a sectional side view of the part of the drug delivery device shown in FIG. 2, FIG. 4A through FIG. 4C show the drug delivery device of FIG. 1 or parts thereof, FIG. 5 schematically shows a perspective sectional view of a part of FIG. 4B, FIG. 6 schematically shows a perspective sectional view of another part of FIG. 4B, FIG. 7 schematically shows a perspective sectional view of a part of the drug delivery device of FIG. 1.

In FIG. 1 a drug delivery device 1 is shown. The drug delivery device 1 comprises a cartridge unit 2. The drug delivery device 1 comprises a drive unit 3. The drug delivery device has a housing 11.

The cartridge unit 2 comprises a cartridge holder 39. The cartridge unit 2 comprises a cartridge 4. The cartridge 4 is, preferably releasably, secured to the cartridge holder 39. The cartridge holder 39 stabilizes the cartridge 4 mechanically.

The cartridge 4 may hold a plurality of doses of a drug 5. The drug 5 is preferably a liquid medication, comprising, for example, insulin, like short-acting or long acting-insulin, heparin or growth hormones.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)-4-des Pro36, des Pro37 Exendin-4(1-39)-NH2,
H-(Lys)-5-des Pro36, des Pro37 Exendin-4(1-39)-NH2,
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39); or
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39),
wherein the group-Lys6-NH2 may be bound to the C-terminus of the Exendin-4 derivative;
or an Exendin-4 derivative of the sequence
H-(Lys)-6-des Pro36 [Asp28]Exendin-4(1-39)-Lys6-NH2,
des Asp28 Pro36, Pro37, Pro38Exendin-4(1-39)-NH2,
H-(Lys)-6-des Pro36, Pro38 [Asp28]Exendin-4(1-39)-NH2,
H-Asn-(Glu)5des Pro36, Pro37, Pro38 [Asp28]Exendin-4(1-39)-NH2,
des Pro36, Pro37, Pro38[Asp28]Exendin-4(1-39)-(Lys)6-NH2,
H-(Lys)-6-des Pro36, Pro37, Pro38[Asp28]Exendin-4(1-39)-(Lys)6-NH2,
H-Asn-(Glu)-5-des Pro36, Pro37, Pro38[Asp28]Exendin-4(1-39)-(Lys)6-NH2, H-(Lys)-6-des Pro36[Trp(O2)25, Asp28]Exendin-4(1-39)-Lys6-NH2, H-des Asp28 Pro36, Pro37, Pro38[Trp(O2)25]Exendin-4(1-39)-NH2, H-(Lys)-6-des Pro36, Pro37, Pro38[Trp(O2)25, Asp28]Exendin-4(1-39)-NH2, H-Asn-(Glu)-5-des Pro36, Pro37, Pro38[Trp(O2)25, Asp28]Exendin-4(1-39)-NH2, des Pro36, Pro37, Pro38[Trp(O2)25, Asp28]Exendin-4(1-39)-(Lys)6-NH2, H-(Lys)-6-des Pro36, Pro37, Pro38[Trp(O2)25, Asp28]Exendin-4(1-39)-(Lys)6-NH2, H-Asn-(Glu)-5-des Pro36, Pro37, Pro38[Trp(O2)25, Asp28]Exendin-4(1-39)-(Lys)6-NH2, H-(Lys)-6-des Pro36[Met(O)14, Asp28]Exendin-4(1-39)-Lys6-NH2, des Met(O)14 Asp28 Pro36, Pro37, Pro38 Exendin-4(1-39)-NH2, H-(Lys)-6-desPro36, Pro37, Pro38[Met(O)14, Asp28]Exendin-4(1-39)-NH2, H-Asn-(Glu)-5-des Pro36, Pro37, Pro38[Met(O)14, Asp28]Exendin-4(1-39)-NH2, des Pro36, Pro37, Pro38[Met(O)14, Asp28]Exendin-4(1-39)-(Lys)6-NH2, H-(Lys)-6-des Pro36, Pro37, Pro38[Met(O)14, Asp28]Exendin-4(1-39)-(Lys)6-NH2, H-Asn-(Glu)$_5$ des Pro36, Pro37, Pro38[Met(O)14, Asp28]Exendin-4(1-39)-(Lys)6-NH2, H-Lys6-des Pro36 [Met(O)14, Trp(O2)25, Asp28]Exendin-4(1-39)-Lys6-NH2, H-des Asp28 Pro36, Pro37, Pro38[Met(O)14, Trp(O2)25]Exendin-4(1-39)-NH2, H-(Lys)-6-des Pro36, Pro37, Pro38[Met(O)14, Asp28]Exendin-4(1-39)-NH2, H-Asn-(Glu)-5-des Pro36, Pro37, Pro38[Met(O)14, Trp(O2)25, Asp28]Exendin-4(1-39)-NH2, des Pro36, Pro37, Pro38[Met(O)14, Trp(O2)25, Asp28]Exendin-4(1-39)-(Lys)6-NH2, H-(Lys)-6-des Pro36, Pro37, Pro38[Met(O)14, Trp(O2)25, Asp28]Exendin-4(S1-39)-(Lys)6-NH2, H-Asn-(Glu)-5-des Pro36, Pro37, Pro38[Met(O)14, Trp(O2)25, Asp28]Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 has an outlet 6. The drug 5 can be dispensed from the cartridge 4 through the outlet 6. The outlet 6 may be covered by a membrane. The membrane may protect the drug 5 against external influences during storage of the cartridge 4. The drug delivery device 1 comprises a piston 9. The piston 9 may be retained in the cartridge 4.

The drive unit 3 comprises a piston rod 10. The drive unit 3 comprises a dose part 12. The dose part 12 comprises a dose knob 13.

The drug delivery device 1 and the housing 11 have a distal end and a proximal end. The term "distal end" 7 designates that end of the drug delivery device 1 or a component thereof which is or is to be arranged closest to a dispensing end of the drug delivery device 1. The term "proximal end" 8 designates that end of the device 1 or a component thereof which is or is to be arranged furthest away from the dispensing end of the device 1.

The drug delivery device 1 may be a pen-type device, in particular a pen-type injector. The device 1 may be a disposable or a re-usable device. The device 1 may be configured to dispense fixed doses of the drug 5 or variable, preferably user-settable doses of the drug 5.

The drug delivery device 1 may comprise a needle assembly (not explicitly shown), comprising for example a needle covered by a needle mount, a needle retainer and/or a needle seal. The needle assembly may be releasably attached to the distal end of the cartridge holder 39. The membrane may be pierced by the needle for dispensing a dose of the drug 5. Alternatively, the drug delivery device 1 may be a needle-free device.

The housing 11 may be designed to enable a safe and comfortable handling of the drug delivery device 1. The housing 11 may be configured to house, fix, protect or guide inner components of the drug delivery device 1, e.g. piston rod 10, dose part 12. Preferably, the housing 11 limits or prevents the exposure of the inner components to contaminants such as liquid, dirt or dust. The housing 11 may be a unitary or a multipart component. The housing 11 may comprise a tubular or cylindrical shape, as shown in FIG. 1. Alternatively, the housing 11 may comprise a non-tubular shape.

The piston 9 is retained within the cartridge 4. The piston 9 is movable with respect to the cartridge 4. The piston 9 may seal the cartridge 4 proximally. Movement of the piston 9 in the distal direction with respect to the cartridge 4 causes the drug 5 to be dispensed from the cartridge 4 through the outlet 6.

The piston rod 10 may operate through the housing 11 of the drug delivery device 1. The piston rod 10 may be designed to transfer axial movement through the drug delivery device 1, for example for the purpose of dispensing the drug 5 (see also FIGS. 2 and 3 for more details). In particular, the piston rod 10 may be designed to transfer force to the piston 9, thereby pushing the piston 9 in a distal direction with respect to the housing. In this way, a dose of the drug 5 may be dispensed from the cartridge 4. The size of the dispensed dose is determined by the distance by which the piston 9 is displaced in the distal direction with respect to the housing 11.

A bearing member 38 may be arranged between the piston 9 and the piston rod 10 to advance the piston 9. The bearing member 38 may be displaced together with the piston rod 10 with respect to the housing 11. The piston rod 10 may be rotatable with respect to the bearing member 38.

The piston rod 10 may be made of a flexible or a rigid material. The piston rod 10 may have a circular or a non-circular cross-section. The piston rod 10 may be a simple rod, a lead-screw, a rack, a pinion system or the like. The piston rod 10 may be of unitary or multipart construction.

The cartridge unit 2 and the drive unit 3 may be, preferably releasably, secured to one another. For this purpose, a proximal end of the cartridge unit 2 may be secured to a distal end of the drive unit 3, for example by a threaded connection. If the cartridge unit 2 is releasably secured to the drive unit 3, the device 1 may be a re-usable device. In this case, the cartridge unit 2 may be detached from the drive unit 3 for providing for a new cartridge 4, if all of the doses of the drug 5 have already been dispensed, and re-attached to the drive unit 3 thereafter. If the cartridge unit 2 is irreleasably secured to the drive unit 3 the drug delivery device 1 may be a disposable device.

The drive unit 3 comprises a drive mechanism, which is described in detail in connection with the description of FIGS. 2 and 3. Dose part 12 may be part of the drive mechanism. The dose part 12 may be movable with respect to the housing 11. The dose part 12 may be movable in a proximal direction for setting a dose of the drug 5. The dose part 12 may be movable in the distal direction with respect to the housing 11 for delivering the set dose of the drug 5.

The distance by which the dose part 12 is moved proximally with respect to the housing 11 for setting the dose of the drug 5 may determine a size of the dose of the drug 5. A proximal end position and a distal end position of the dose part 12 with respect to the housing 11 may be determined by a respective stop feature (not explicitly shown) limiting the proximal or distal movement of the dose part 12 with respect to the housing 11. The dose part 12 may comprise the dose knob 13. The dose knob 13 may be configured to be gripped by a user. The dose knob 13 may be secured against movement with respect to the dose part 12.

The drug delivery device 1 may be a manually, in particular a non-electrically, driven device. A, preferably user-applied, force causing the dose part 12 to be moved distally with respect to the housing 11 may be transferred to the piston rod 10 by the drive mechanism, which is described later on in more detail. Preferably, the drive mechanism may be configured to leave the piston rod 10 stationary with respect to the housing 11 when the dose part 12 is moved in the proximal direction with respect to the housing 11.

Figure 2:
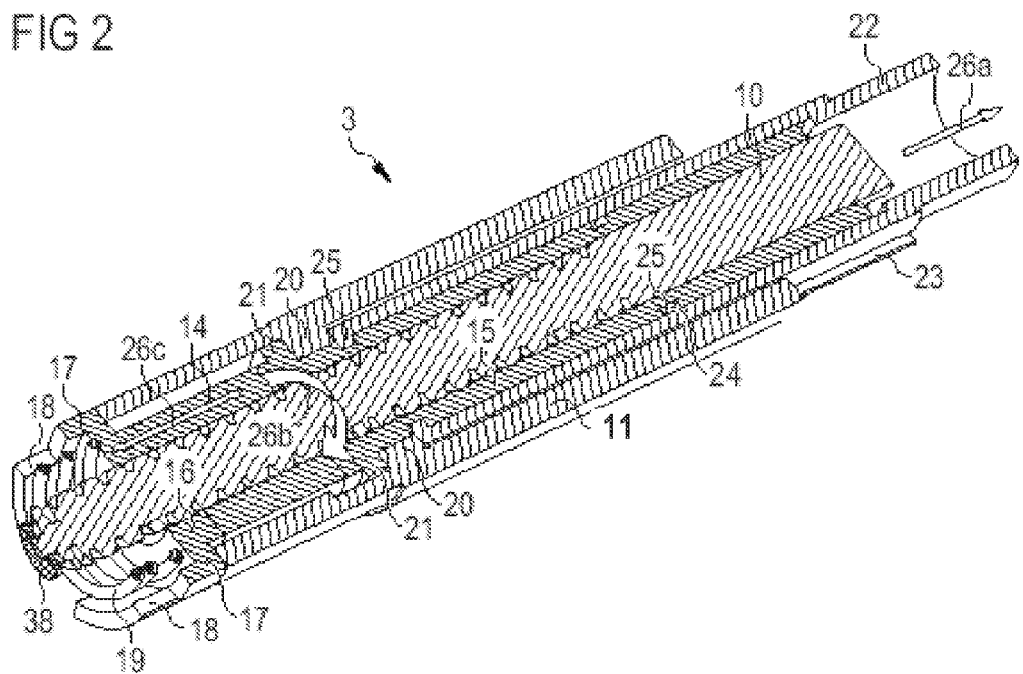

FIG. 2 schematically shows a perspective sectional view of a part of the drug delivery device of FIG. 1. In particular, FIG. 2 illustrates the drive mechanism of the drug delivery device 1, which mechanism was mentioned before.

The drive mechanism comprises a drive member 14. The drive mechanism comprises a rotation member 15. The drive mechanism comprises a stop member 16. The drive mechanism comprises a dose member 22.

Figure 3:
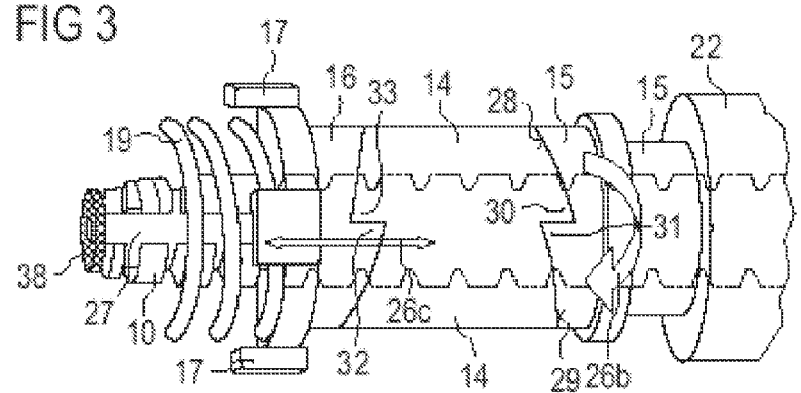

FIG. 3 schematically shows a sectional side view of the part of the drug delivery device shown in FIG. 2.

The drive mechanism is arranged within the housing 11 of the drug delivery device 1. The rotation member 15 is rotatable in a dose setting direction with respect to the housing 11 for setting a dose of the drug 5. The rotation member 15 is rotatable in a dose delivery direction with respect to the housing 11, as indicated by arrow 26b, for delivering the set dose of the drug 5. The dose delivery direction may be opposite to the dose setting direction. The rotation member 15 may comprise an outer thread (see thread 24, FIG. 6).

The rotation member 15 comprises at least one stop feature (see stop feature 36 in FIGS. 4 to 7). The stop feature 36 may be provided within the rotation member 15. Preferably, the rotation member 15 and the stop feature 36 are unitary. The stop feature 36 may be arranged at a distal end section of the rotation member 15. The stop feature 36 may protrude radially inwardly from the rotation member 15. The stop feature may be configured to prevent setting of a dose of the drug 5 which may exceed a present quantity of the drug 5 held in the cartridge 4. Operation of the stop feature 36 will be described in connection with FIGS. 4 to 7.

The drive member 14 is rotatable with respect to the housing 11. The drive member 14 and the rotation member 15 are preferably configured to rotate about a common rotation axis when delivering the set dose. The rotation axis may be a main longitudinal axis of the housing 11. Preferably, the rotation axis runs along the piston rod 10 and, in particular, along a main direction of extent of the piston rod 10.

The rotation member 15 and the drive member 14 are in permanent mechanical contact. The rotation member 15 is coupled to the drive member 14 by a uni-directional clutch mechanism, in particular a friction clutch mechanism, for example a slipping clutch. The clutch mechanism permits rotational movement of the rotation member 15 with respect to the drive member 14 when the rotation member 15 rotates in the dose setting direction with respect to the housing 11, e.g. when setting a dose of the drug. The clutch mechanism prevents rotational movement of the rotation member 15 with respect to the drive member 14, when the rotation member 15 rotates in the dose delivery direction with respect to the housing 11, e.g. when delivering the set dose of the drug 5. Consequently, the drive member 14 follows rotational movement of the rotation member 15 in the dose delivery direction with respect to the housing 11 when delivering the set dose of the drug 5.

The drive member 14 may be arranged to abut or engage the rotation member 15. For engaging the rotation member 15, the drive member 14 comprises a toothing (see toothing 28 in FIG. 3), which may be arranged at the proximal end section of the drive member 14, for example. In addition, the rotation member 15 comprises a toothing (see toothing 29 in FIG. 3), which may be arranged at the distal end section of the rotation member 15, for example. In particular, toothing 29 may be arranged at one end section of the rotation member 15 which faces the drive member 14. Toothing 29 and toothing 28 may be configured to mate with each other. Toothing 28 comprises a plurality of teeth (teeth 30 in FIG. 3). Toothing 29 comprises a plurality of teeth (see teeth 31 in FIG. 3). Teeth 30 and teeth 31 may extend along the rotation axis. The rotation axis may be oriented along the main longitudinal axis of the housing 11.

A respective tooth of teeth 30 and teeth 31 may be ramp-shaped, in particular along an azimuthal direction with respect to the rotation axis. The ramp of the respective tooth 30, 31 is limited in the azimuthal direction by a steep end face of said tooth, e.g. a face of the tooth 30, 31 that runs parallel to the rotation axis. When the steep end faces of two teeth 30, 31 abut and the rotation member 15 is rotated further in the dose delivery direction with respect to the housing 11, the steep sides stay in abutment and hence, the drive member 14 follows rotation of the rotation member 15. When the rotation member 15 rotates in the dose setting direction with respect to the housing 11, the ramps of the teeth 30 31 slide along each other and hence, the rotation member 15 rotates with respect to the drive member 14.

The depth of a tooth 30, 31 of the respective toothing 28, 29 determines the distance by which the rotation member 15 is axially moveable with respect to the housing 11. In particular, axial movement of the rotation member 15 with respect to the housing 11 is prevented, e.g. by mechanical cooperation of the rotation member 15 and the housing 11, in case that the axial distance exceeds the depth of a respective tooth 30, 31 of toothings 28, 29.

The drive member 14 may engage the piston rod 10. The drive member 14 may be splined to the piston rod 10. Preferably, the piston rod 10 comprises a guide notch (see guide notch 27, FIGS. 5 and 7). The drive member 14 may comprise a corresponding guide rib (not explicitly shown) for engaging the guide notch. Preferably, the guide rib extends inside the drive member 14 along the main longitudinal axis of the housing 11. The corresponding guide notch 27 may extend at an outer side of the piston rod 10 along the main longitudinal axis of the piston rod 10. The splined connection of the drive member 14 and the piston rod 10 prevents relative rotational movement of the drive member 14 with respect to piston rod 10 and vice versa. Hence, the drive member 14 and the piston rod 10 are permanently rotationally locked.

The drive member 14 is configured to transfer force, preferably torque, to the piston rod 10. The force transferred may cause the piston rod 10 to be rotated with respect to the housing 11. Additionally or alternatively, the force transferred may cause the piston rod 10 to be displaced in the distal direction with respect to the housing 11 for delivering a dose of the drug 5.

Figure 4:
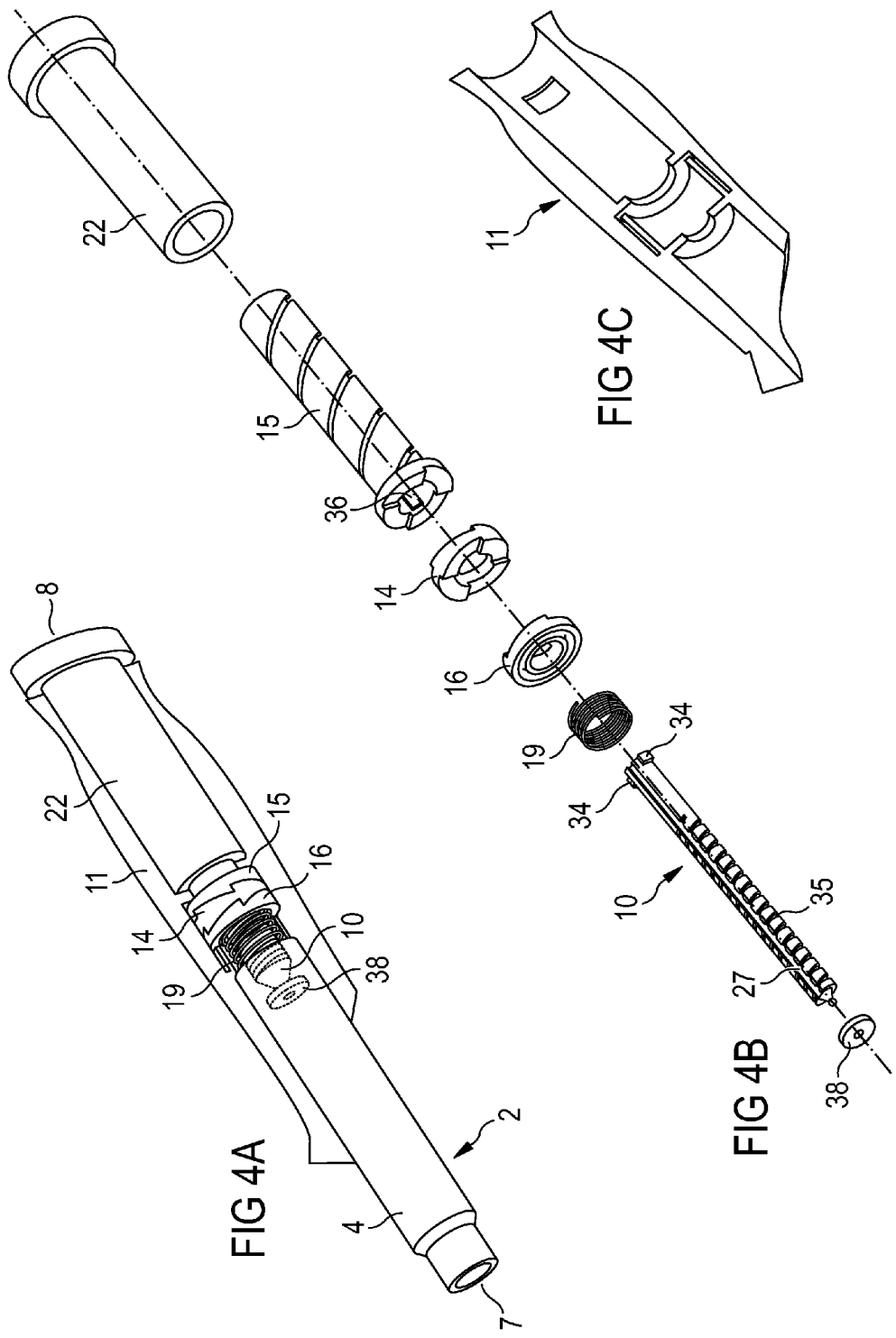
Figure 5:
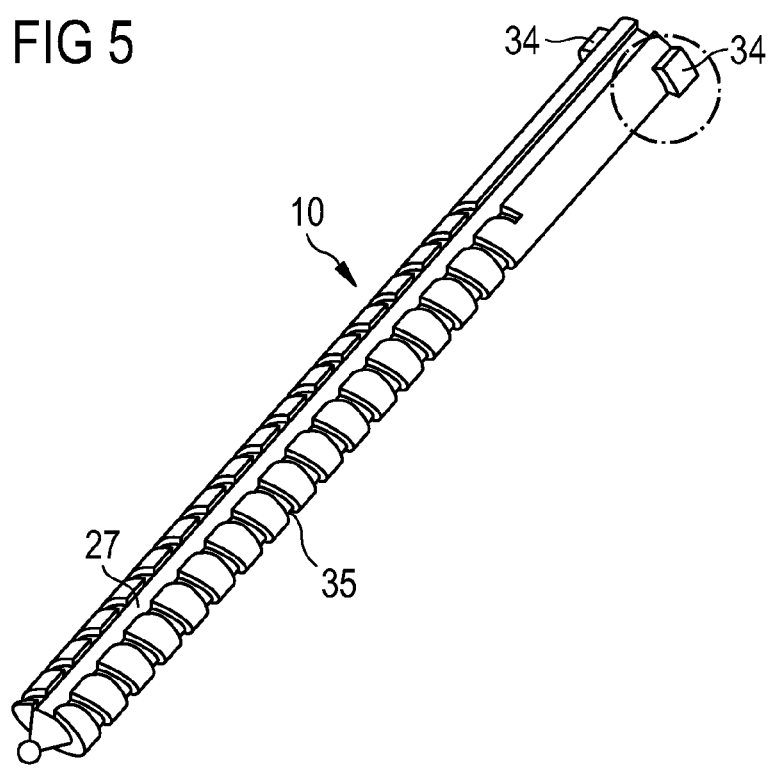
Figure 7:
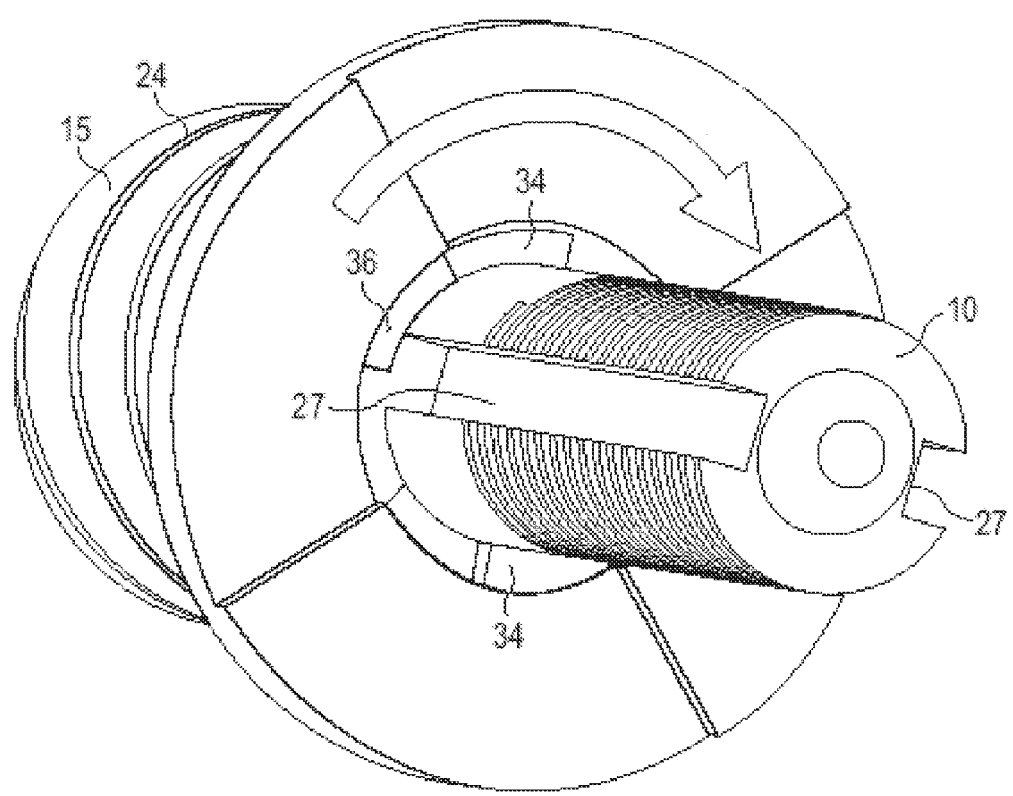

The piston rod 10 comprises a thread (see thread 35, FIGS. 4, 5 and 7). The thread 35 may be arranged at an outer surface of the piston rod 10. A counterpart, e.g. a further thread, may be provided inside the housing 11 for a threaded engagement of the housing 11 and piston rod 10. Rotational movement of the piston rod 10 may be converted into axial movement of the piston rod 10 in the distal direction with respect to the housing 11 due to the threaded engagement of the piston rod 10 and the housing 11.

The drive member 14 may be arranged between the stop member 16 and the rotation member 15. The stop member 16 is configured to prevent rotational movement of the drive member 14 in the dose setting direction with respect to the housing 11 when setting the dose of the drug 5. Consequently, when setting the dose, the rotation member 15 rotates with respect to the drive member 14 and with respect to the stop member 16. The stop member 16 is preferably secured against rotation with respect to the housing 11. The stop member 16 may be splined to the housing 11.

The stop member 16 may be coupled to the drive member 14 by means of a uni-directional clutch mechanism. The clutch mechanism prevents rotational movement of the drive member 14 with respect to the stop member 16 when the rotation member 15 rotates in the dose setting direction with respect to the housing, e.g. when setting the dose of the drug 5. The clutch mechanism permits rotational movement of the drive member 14 with respect to the stop member 16 when the rotation member 15 rotates in the dose delivery direction with respect to the housing 11, e.g. when delivering the set dose of the drug 5.

The stop member 16 may be arranged to abut or engage the drive member 14, preferably when setting and when delivering the set dose. The stop member 16 comprises a toothing (see toothing 32 in FIG. 3) at one end section which faces the drive member 14, for example the proximal end section of the stop member 16. The teeth of toothing 32 may be ramp-shaped and may be disposed along a perimeter of the drive member 14.

The drive member 14 comprises a toothing (see toothing 33 in FIG. 3), preferably at the distal end section of the drive member 14. Thereby, toothing 28 and toothing 33 of the drive member 14 are disposed oppositely. Toothing 33 may be configured in accordance with toothing 29 of the rotation member 15. Toothing 32 and toothing 33 may be configured to cooperate for preventing rotation of the drive member 14 with respect to the housing 11 and with respect to the stop member 16 when setting the dose of the drug 5.

As rotation of the drive member 14 in the dose setting direction with respect to the housing 11 is prevented, movement of the piston rod 10 in the proximal direction with respect to the housing 11 as well as rotation of the piston rod 10 in the dose setting direction with respect to the housing 11 during setting of the dose is prevented.

As mentioned previously, stop member 16 may be secured against rotational movement with respect to the housing 11. However, stop member 16 may be axially displaceable with respect to the housing 11, as indicated by arrow 26c in FIG. 3. For this purpose, the stop member 16 may comprise a plurality of guiding members, for example guide lugs 17. Guide lugs 17 may engage with corresponding guide slots 18. The guide slots 18 may be provided in the housing 11. A guide lug 17 cooperates with a guide slot 18 to prevent rotational movement of the stop member 16 with respect to the housing 11 with distal movement of the stop member 16 with respect to the housing 11 being allowed.

The drive mechanism further comprises a resilient member 19, for example a spring member. The resilient member 19 may be biased during dose delivery. The resilient member 19 may provide a force keeping the drive member 14 in permanent mechanical cooperation, e.g. engagement, with the stop member 16 and the rotation member 15, when setting and delivering a dose.

The drive mechanism comprises a support member 20. The support member 20 may be secured against axial and rotational movement with respect to the housing 11. The support member 20 may be unitary with the housing 11. The support member 20 may be a protrusion, for example. The rotation member 15 may extend through an opening in support member 20. Support member 20 may provide a counter force to the force exerted by the resilient member 19.

The rotation member 15 comprises a protruding portion 21. The protruding portion 21, e.g. a flange portion, may protrude radially outwardly with respect to the rotation member 15. The protruding portion 21 may be configured to abut support member 20. The protruding portion 21 prevents proximal displacement of the rotation member 15 with respect to the housing 11.

The dose member 22 may be a part of the dose part 12 (see FIG. 1) or operatively connected to the dose part 12. The rotation member 15 may be arranged inside the dose member 22. Dose member 22 may be movable with respect to the housing 11. Dose member 22 may be moved in the proximal direction with respect to the rotation member 15 and with respect to the housing 11 when setting a dose, which is indicated by arrow 26a in FIG. 2. Dose member 22 may be moved in the distal direction with respect to the rotation member 15 and with respect to the housing 11 for delivering the set dose. The dose member 22 may engage the housing 11. Preferably, the dose member 22 is secured against rotation with respect to the housing 11. The dose member 22 may comprise a guide feature 23, for example a guide slot, engaging with another guide feature (not explicitly shown in FIG. 2 and FIG. 3), for example a guide lug, which may be provided in the housing 11.

The dose member 22 may be coupled to, preferably threadedly engaged with, the rotation member 15. For this purpose, the rotation member 15 may comprise the outer thread 24. The dose member may comprise a thread 25. Thread 25 may be provided inside the dose member 22. Thread 24 may be engaged with thread 25. The dose member 22 and the rotation member 15 may be threadedly engaged such that axial movement of the dose member 22 may be converted into rotational movement of the rotation member 15. Thus, movement of the dose member 22 in proximal direction with respect to the housing 11 when setting a dose may be converted into rotation of the rotation member 15 in the dose setting direction with respect to the housing 11. Movement of the dose member 22 in the distal direction with respect to the housing 11 when delivering the set dose may be converted into rotation of the rotation member 15 in the dose delivery direction with respect to the housing 11.

The drive member 14, the rotation member 15, the stop member 16 and the dose member 22 may comprise or may be embodied as a sleeve, respectively. The piston rod 10 may be arranged and/or driven through at least one, or more or all of said sleeves.

FIG. 4A through 4C show the drug delivery device of FIG. 1 or parts thereof. In particular, FIG. 4A shows an inner view of the drug delivery device 1. FIG. 4B shows an exploded view of the drug delivery device 1. FIG. 4C shows an inner view of the housing 11.

The rotation member 15 comprises the stop feature 36 as mentioned previously. Alternatively, the rotation member may comprise two or more stop features 36. The stop feature 36 is localized at the distal end section of the rotation member 15. The stop feature 36 is provided inside the rotation member 15.

The stop feature 36 is preferably arranged at a distal end section of the rotation member 15. Preferably, the stop feature 36 is arranged inside the rotation member 15. Preferably, the stop feature 36 protrudes radially inwardly from the rotation member 15. The stop feature 36 is preferably integrally formed with the rotation member 15. Alternatively, a separate stop feature 36 may be connected to the rotation member 15. Preferably, the stop feature 36 is secured against translational and rotational movement with respect to the rotation member 15.

The piston rod 10 comprises two blocking members 34. The blocking members 34 may be arranged in a proximal end section of the piston rod 10. The blocking members 34 may be oppositely arranged. Alternatively, the piston rod 10 may comprise only one blocking member 34. Alternatively, the piston rod may 10 comprise three or more blocking members 34.

Preferably, the blocking members 34 are integrally formed with the piston rod 10. Alternatively, the blocking members 34 may be connected to the piston rod 10. The blocking members 34 may protrude radially outwardly from the piston rod 10. Preferably, the blocking members 34 are secured against translational and rotational movement with respect to the piston rod 10.

The stop feature 36 rotates together with the rotation member 15 in the dose setting direction with respect to the blocking members 34 and with respect to the housing 11 for setting a dose. Thereby, the stop feature 36 may be rotated about a stop feature angle in the dose setting direction. Preferably, the stop feature 36 is rotated by less than 360 degrees in the dose setting direction with respect to the blocking members 34. The blocking members 34 may be secured against rotation in the dose setting direction with respect to the housing 11 as the piston rod 10 is prevented from being rotated in the dose setting direction with respect to the housing 11, as it was described previously.

The stop feature 36 may be rotated about a stop feature angle of 90 degrees, for example, for setting a dose of the drug 5. As being part of the rotation member 15 significant axial displacement of the stop feature 36, or any axial displacement, with respect to the housing 11 may be prevented, when setting and delivering a dose.

The stop feature 36 rotates together with the rotation member 15 in the dose delivery direction for delivering the set dose of the drug 5. Accordingly, the blocking members 34 rotate together with the piston rod 10 in the dose delivery direction for delivering the set dose of the drug 5. Thus, the stop feature 36 is configured to be rotated together with the blocking members 34 in the dose delivery direction with respect to the housing 11. The blocking members 34 may rotate with respect to the stop feature 36.

The blocking members 34 are configured to be displaced together with the piston rod 10 in the distal direction with respect to the housing 11 for delivering the set dose of the drug 5, thereby being axially displaced with respect to the stop feature 36. The blocking members 34 may be axially displaced from an axial starting position and towards an axial interaction position. In the axial starting position the blocking members 34 may be axially offset from the stop feature 36. In the axial interaction position the blocking members 34 may overlap with the stop feature 36.

When the blocking members 34 are out of the axial interaction position, e.g. when the blocking members 34 are in the axial starting position, the stop feature 36 may pass an angular position of the blocking members 34 while being rotated about the stop feature angle. Hence, when the blocking members 34 are not positioned in the axial interaction position, the stop feature 36 may be rotatable about at least a minimum stop feature angle, e.g. the angle required for completion of a dose setting action, e.g. 90 degrees, in the dose setting direction with respect to the housing 11 for setting a dose.

The blocking members 34 may be rotated about a blocking member delivery angle in the dose delivery direction with respect to the housing 11 when being displaced from the axial starting position towards the axial interaction position.

Preferably, the blocking members 34 are rotated by 360 degrees or more in the dose delivery direction with respect to the housing 11 when being displaced from the axial starting position towards the axial interaction position.

Preferably, when a last dose has been delivered, e.g. when a subsequent minimum settable dose of the drug 5 would exceed the quantity of the drug 5 still present in the cartridge 4, the blocking members 34 have been axially displaced with respect to the stop feature 36 such that the blocking members 34 are positioned in the axial interaction position, e.g. the blocking members 34 overlap the stop feature 36. Preferably, the total axial displacement distance of the blocking members 34 from the axial starting position into the axial interaction position corresponds to the total amount of the drug 5 held in the cartridge 4.

The axial interaction position may be defined by the axial position of the stop feature 36 with respect to the housing 11. Hence, when the blocking members 34 have reached the axial position of the stop feature 36 the blocking members 34 are in the axial interaction position.

The drive mechanism may be configured such that axial displacement of the piston rod 10 for delivering the set dose results in the blocking members 34 being in the axial interaction position when the distal end position of the piston rod 10 was reached. In particular, the outer thread 35 of the piston rod 10 and the inner thread of the housing 11 may be adapted such that the blocking members 34 overlap with the stop feature 36 when the piston rod 10 has reached the distal end position, e.g. when the piston 9 has reached the most distal position in the cartridge 4.

When the blocking members 34 are in the axial interaction position the angular distance between the blocking members 34 and the stop feature 36 is expediently less than the stop feature angle. In particular, the minimum rotation angle of the stop feature 36 necessary for setting a minimum dose may be greater than the angular distance between the stop feature 36 and the blocking members 34. Hence, a further dose setting action is prevented when the blocking members 34 are in the axial interaction position.

In this way, the stop feature 36 and the blocking members 34 provide an end-stop mechanism for the drug delivery device 1. Setting of a dose of the drug 5 which exceeds a quantity of the drug 5 still held in the cartridge 4 is thus effectively prevented. In this way, underdosing, which may have fatal or even lethal consequences for the user, may be prevented.

FIG. 5 schematically shows a perspective sectional view of a part of FIG. 4B. In particular, FIG. 5 shows the piston rod 10 comprising the two blocking members 34. The blocking members 34 are disposed oppositely and protrude radially outwardly from the piston rod 10 as described above.

The piston rod 10 may comprise guide notch 27. Guide notch 27 may enable splined connection of the piston rod 10 with the drive member 14 as described in connection with the description of FIGS. 2 and 3. Preferably, the piston rod 10 comprises two guide notches 27. The guide notches 27 may be arranged oppositely (see FIG. 7). In addition, the piston rod 10 comprises the outer thread 35. Outer thread 35 may enable threaded connection of the piston rod 10 with the housing 11, as explained in conjunction with the description of FIG. 1.

Figure 6:
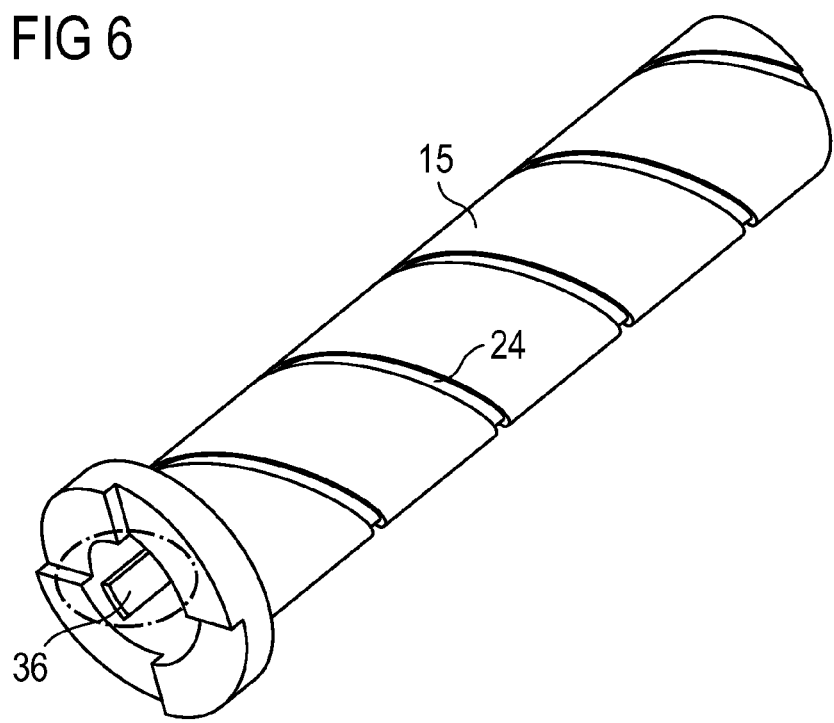

FIG. 6 schematically shows a perspective sectional view of another part of FIG. 4B. In particular, FIG. 6 shows the rotation member 15. The rotation member 15 comprises the stop feature 36. The stop feature 36 protrudes radially inwardly from the rotation member 15.

The rotation member 15 comprises thread 24. Thread 24 may enable threaded engagement of the rotation member 15 and the dose member 22 as mentioned previously.

FIG. 7 schematically shows a sectional view of a part of the drug delivery device of FIG. 1. In particular, FIG. 7 shows mechanical cooperation of the stop feature 36 and the stop members 34.

A last dose of the drug 5 held in the cartridge 4 may have been dispensed, i.e. the piston 9 may have reached the most distal end position in the cartridge 4, and thus, the blocking members 34 are positioned in the axial interaction position. As shown in FIG. 7 the blocking members 34 and the stop feature 36 mechanically cooperate, in particular overlap, in the interaction position. Rotation of the stop feature 36 and hence, of the rotation member 15 may be prevented in this way as described in connection with FIG. 4. Thus, setting of a subsequent dose of the drug 5 may be prevented.

The device 1 effectively prevents setting of a dose of the drug 5 which exceeds the present quantity of the drug 5 held in the cartridge 4. Hence, the device 1 provides an end-stop mechanism. In this way, underdosing, which may have fatal or lethal consequences for the user, may be prevented. Consequently, the drug delivery device 1 described herein provides an increased safety for the user.

Preferably, the device 1 is a fixed dose drug delivery device, e.g. a device configured to dispense a plurality of pre-set doses of the drug 5, in particular doses which may not be varied by the user. In this case, the angle by which the stop feature 36 is rotated in the dose setting direction for setting a dose of the drug, i.e. the stop feature angle, may be the same for each dose setting action.

Other implementations are within the scope of the following claims. Elements of different implementations may be combined to form implementations not specifically described herein.

The invention claimed is:

1. An assembly for a drug delivery device, comprising:
   a housing,
   at least one stop feature,
   at least one blocking member,
   a piston rod configured to be axially displaced with respect to the housing for delivering a dose of a drug, wherein blocking member is part of the piston rod,
   a rotation member, wherein the stop feature is part of the rotation member and wherein the rotation member is configured to rotate in a dose setting direction with respect to the housing for setting a dose of the drug and to rotate in a dose delivery direction with respect to the housing for delivering the set dose of the drug, and
   a rigid drive member which is adapted to follow rotational movement of the rotation member in the dose delivery direction with respect to the housing by mechanical interaction with the rotation member, wherein the rigid drive member and the piston rod are rotationally locked with each other,
   wherein for setting the dose of the drug, the stop feature is configured to be rotated in the dose setting direction with respect to the blocking member and with respect to the housing and, for delivering the set dose of the drug, the blocking member is configured to be axially displaced with respect to the stop feature away from an axial starting position and towards an axial interaction position, wherein,
   when the blocking member is in the axial starting position, the blocking member is axially offset from the stop feature and, when the blocking member is in the axial interaction position, the blocking member is configured to mechanically cooperate with the stop feature such that rotation of the stop feature in the dose setting direction with respect to the housing is prevented,
   wherein the assembly comprises a stop member rotationally fixed to the housing that prevents rotational movement of the rigid drive member by engagement of a unidirectional clutch in the dose setting direction with respect to the housing by mechanical cooperation with the rigid drive member when the rotation member is rotated in the dose setting direction with respect to the housing.

2. The assembly of claim 1, wherein for delivering the set dose of the drug the blocking member and the stop feature are configured to rotate together in the dose delivery direction with respect to the housing.

3. The assembly of claim 1, wherein the blocking member is secured against rotation in the dose setting direction with respect to the housing as the piston rod is prevented from being rotated in the dose setting direction with respect to the housing such that common rotation of the blocking member and the stop feature in the dose setting direction with respect to the housing is prevented when the blocking member and the stop feature mechanically cooperate with each other.

4. The assembly according to claim 1, wherein the stop feature is configured to be rotated about a stop feature angle in the dose setting direction with respect to the housing for setting a dose of the drug and the blocking member is configured to be rotated about a blocking member delivery angle in the dose delivery direction with respect to the housing when the blocking member is displaced from the axial starting position towards the axial interaction position, and wherein, when the blocking member is in the axial interaction position, the angular distance between the blocking member and the stop feature is less than the stop feature angle.

5. The assembly according to claim 1, wherein the stop feature is configured to be rotated by less than 360 degrees in the dose setting direction with respect to the housing for setting a dose of the drug.

6. The assembly according to claim 1, wherein the blocking member is configured to be rotated by 360 degrees or more in the dose delivery direction with respect to the housing when being displaced from the axial starting position towards the axial interaction position.

7. The assembly according to claim 1, wherein, when the blocking member is out of the axial interaction position, the stop feature is configured to pass an angular position of the blocking member for setting a dose of the drug.

8. The assembly according to claim 1, wherein the axial interaction position is defined by an axial position of the stop feature with respect to the housing.

9. The assembly according to claim 1, wherein the piston rod is configured to be axially displaced with respect to the housing for delivering the set dose of the drug.

10. The assembly according to claim 9, wherein rotation of the rigid drive member in the dose delivery direction with respect to the housing is converted into axial movement of the piston rod with respect to the housing.

11. The assembly according to claim 1, wherein the stop feature radially protrudes from the rotation member and the blocking member radially protrudes from the piston rod.

12. The assembly according to claim 1, wherein, when the blocking member and the stop feature mechanically cooperate in the axial interaction position, completion of a further dose setting action is prevented.

13. The assembly according to claim 1, comprising at least two oppositely disposed blocking members.

14. A drug delivery device comprising the assembly according to claim 1, further comprising a cartridge, the cartridge holding a plurality of doses of the drug, wherein the assembly provides an end-stop mechanism for the drug delivery device which is configured to prevent setting of a dose of the drug which exceeds a quantity of the drug present in the cartridge.

* * * * *